United States Patent

Nakacho et al.

Patent Number: 4,724,264

Date of Patent: Feb. 9, 1988

[54] FLUOROALKOXY CYCLIC PHOSPHONITRILE ESTERS

[75] Inventors: Yoshifumi Nakacho; Yuji Tada, both of Tokushima; Tetsuya Yagi, Ibaraki, all of Japan

[73] Assignees: Otsuka Kagaka Kabushiki Kaisha, Osaka; Matsumura Oil Research Corporation, Hyogo, both of Japan

[21] Appl. No.: 856,360

[22] Filed: Apr. 28, 1986

[30] Foreign Application Priority Data

Apr. 30, 1985 [JP] Japan .................................. 60-94296

[51] Int. Cl.$^4$ .............................................. C07F 9/00
[52] U.S. Cl. .................................................... 558/80
[58] Field of Search ......................................... 558/80

[56] References Cited

U.S. PATENT DOCUMENTS 3,888,800 6/1975 Allcock ................................ 558/80
4,601,843 7/1986 Carr et al. .............................. 558/80

OTHER PUBLICATIONS

Austin et al, "Macromolecules", (1983), 16, 719–722.

Primary Examiner—Anton H. Sutto
Attorney, Agent, or Firm—Murray and Whisenhunt

[57] ABSTRACT

A fluoroalkoxy cyclic phosphonitrile ester represented by the formula (1)

$$[H(CF_2CF_2)_mCH_2O]_{2n-l}[CF_3CF_2CH_2O]_lP_nN_n \quad (1)$$

wherein $(CF_2CF_2)m$ is a single segment of the unit $(CF_2CF_2)$ multiplied by an integer or indicates conjoint presence of segments having different chain lengths and each comprising the unit $(CF_2CF_2)$ multiplied by an integer, m is 2 in the case of the single segment or, in the case of the presence of segments of different chain lengths, represents the average of the chain lengths, means the average number of repeating units $(CF_2CF_2)$ and is in the range of $1.3 \leq m \leq 2.8$, l is in the range of $2n-1 \geq l \geq 1$, and n is the number of repeating PN units of the phosphonitrile cyclic skeleton, or represents the average number of repeating PN units and is a real number in the range of $3 \leq n \leq 4.3$ when rings of different numbers of repeating units are conjointly present.

2 Claims, 9 Drawing Figures

FLUOROALKOXY CYCLIC PHOSPHONITRILE ESTERS

The present invention relates to novel fluoroalkoxy cyclic phosphonitrile esters.

Petroleum lubricant heretofore widely used as rotary pump oil is prepared from a petroleum lubricant fraction having a kinematic viscosity of 30 to 150 centistokes at 40° C., by refining the fraction by fractionation such as molecular distillation. The lubricant is very low in vapor pressure, has high heat resistance and meets various requirements.

In recent years, however, improved properties are required of rotary pump oil with a trend to use a vacuum for wider application, so that the petroleum rotary pump oil often fails to meet the requirements. Especially because vacuums have found wider use in thin film production techniques, it has been highly desired to provide a rotary pump oil having high resistance to active gases such as halogen compounds. For example, the rotary pump oil for the dry etching apparatus for producing semiconductors is exposed to an active gas such as a gas mixture of tetrafluoromethane (Flon-14) and oxygen, so that the conventional petroleum rotary pump oil, if used, is prone to a rise of viscosity or deposition of sludge within a short period of time, therefore needs frequent replacement and requires much time and labor for the maintenance of the rotary pump.

Accordingly, there is a strong demand for a rotary pump oil which is resistant to such active gases.

The apparatus which are presently used and in which an active gas is used or needs to be discharged include dry etching apparatus, semiconductor manufacturing apparatus which are typicallly used for ion implantation apparatus and plasma chemical vapor deposition (CVD) apparatus, CVD apparatus for producing cutting tools of cemented carbides, apparatus for producing halogen lamps, degassing apparatus for preparing iron and steel, and apparatus for producing electrically superconductive materials.

Examples of active gases which are used are phosphine, arsine, diborane, hydrogen selenide, arsenic trichloride, silane, silicon tetrachloride, hydrogen chloride, dichlorosilane, Flon-14, ammonia, phosphorus pentafluoride, silicon tetrafluoride, carbon tetrachloride and oxygen. These gases are used singly, or at least two of them are used in combination.

When used for the conventional pumps of the above apparatus, rotary pump oil markedly deteriorates owing to reaction with the active gas. For example, when exposed to a chlorine-containing active gas, the pump oil reduces in viscosity. In the case of a fluorine-containing gas, the viscosity rises conversely or deposition of sludge occurs. Thus, it is desired to develop a novel pump oil having high resistance to active gases and substituting for the conventional oil which is not usable for a long period of time. Especially very intricate difficulties are involved in the problem of balance between the properties required of the rotary pump oil. Especially, the oil must have a very low viscosity, a low vapor pressure, the satisfactory low-temperature characteristic of being minus tens of degrees in solidifying point, and heat resistance to withstand the heat developed from the operation of the pump, and all of these requirements need to be fulfilled by a single chemical structure. In other words, these are characteristics which conflict with one another and nevertheless need to be realized at the same time. For example, a reduced molecular weight provides a lower viscosity but results in a higher vapor pressure. Attempts to obtain low-temperature characteristics tend to lower the upper limit of temperatures where satisfactory oil properties are available. Thus, difficulties are encountered in molecular design. Moreover, the chemical substance obtained with these characteristics must further have exceedingly high stability against chemical substances such as acids and alkalis, especially active gases. Extreme difficulties are therefore encountered in preparing a novel chemical substance having all of these required characteristics in good balance.

From such a viewpoint, we have already developed a fluorophosphonitrilate oil which is satifactorily usable for the above application (see Japanese Unexamined Patent Publication No. 1983-164698). However, the fluorophosphonitrilate oil still remains to be improved in heat resistance, viscosity and compatibility with resins although outstanding in performance as a lubricant and in resistance to active gases.

An object of the invention is to provide a compound which is excellent in heat resistance, viscosity, compatibility with resins and low-temperature characteristics, as well as in lubricant performance and resistance to active gases.

The above and other objects of the invention will become apparent from the following description.

The present invention provides a fluoroalkoxy cyclic phosphonitrile ester represented by the formula (1)

wherein $(CF_2CF_2)m$ is a single segment of the unit $(CF_2CF_2)$ multiplied by an integer or indicates conjoint presence of segments having different chain lengths and each comprising the unit $(CF_2CF_2)$ multiplied by an integer, m is 2 in the case of the single segment or, in the case of the presence of segments of different chain lengths, represents the average of the chain lengths, means the average number of repeating units $(CF_2CF_2)$ and is in the range of $1.3 \leq m \leq 2.8$, l is in the range of $2n - 1 \geq l \geq 1$, and n is the number of repeating PN units of the phosphonitrile cyclic skeleton, or represents the average number of repeating PN units and is a real number in the range of $3 \leq n \leq 4.3$ when rings of different numbers of repeating units are conjointly present.

The fluoroalkoxy cyclic phosphonitrile ester of the formula (1) is a novel compound not disclosed in literature and is prepared from an oligomer of phosphonitrile halide and a fluoroalcohol as described in the example given later. Namely, the cyclic phosphonitrile ester of the formula (1) is prepared by reacting an oligomer of phosphonitrile halide of the formula

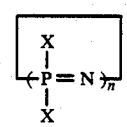

wherein X is halogen atom, n represents the average number of repeating PN units and is a real number in the range of $3 \leq n \leq 4.3$ when rings of different numbers of repeating units are conjointly present, a fluoroalcohol of the formula

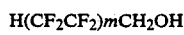

and a fluoroalcohol of the formula $$CF_3CF_2CH_2OH$$

wherein m means the average number of repeating units ($CF_2CF_2$) and is in the range of $1.3 \leq m \leq 2.8$.

Examples of useful oligomers of phosphonitrile halides are phosphonitrile chloride trimer, phosphonitrile chloride tetramer and a mixture of such oligomers. Examples of useful fluoroalcohols are 1,1,3-trihydroperfluoropropanol, 1,1,5-trihydroperfluoropentanol and like 1,1,ω-trihydroperfluoroalcohols, mixtures of such an alcohol and 2,2,3,3,3-pentafluoropropanol. Alternatively, the fluoroalkoxy cyclic phosphonitrile ester of the formula (1) is prepared by reacting sodium or like alkali metal with a mixture of at least one 1,1,ω-trihydroperfluoroalcohols and 2,2,3,3,3-pentafluoropropanol to obtain an alcoholate and subsequently reacting the alcoholate with an oligomer of phosphonitrile halide.

In the reaction of phosphonitrile halide oligomer and fluoroalcohol, the latter is usually used in an amount of about 2.02 to 2.25 moles per one unit mole of the former as calculated in terms of $PNX_2$. Further, the fluoroalcohol is preferably converted into an alcoholate beforehand by the reaction thereof with sodium or like alkali metal. The reaction is conducted preferably in an organic solvent such as benzene, toluene, xylene and like hydrocabons, ethyl ether, isopropyl ether, tetrahydrofuran, dioxane and like ethers, etc. The reaction temperature is preferably from about 10° C. to reflux temperature, and particularly from room temperature to 100° C. The reaction time is not particularly determined but is preferably about 2 to 10 hours.

The present desired compound can be isolated and purified by a known method and for example is washed with water, dried, concentrated and then purified by a precision fractionator, etc.

Among the fluoroalkoxy cyclic phosphonitrile esters represented by the formula (1), preferable are, for example, mixed fluoroalkoxytetraphosphonitrilates of the formula (1) wherein n is 4, m is 2 and l is in the range of $1 \leq l \leq 7$.

The compounds of the present invention are useful as nonflammable lubricants, hydraulic oils, etc., especially as rotary pump oils.

When l is 0, the ester has a high viscosity at room temperature and requires an excessively great torque for starting pumps, possibly causing damage to the electric motor. If l is 8, the ester is solid at room temperature and is unusable as a fluid. Accordingly, such esters are not suited to use.

The present invention will be described in greater detail with reference to the following examples and reference examples.

EXAMPLE 1

Into a four-necked flask equipped with a condenser, stirrer and thermometer were placed 310 g (2.06 moles) of 2,2,3,3,3-pentafluoropropanol, 480 g (2.06 moles) of 1,1,5-trihydroperfluoropentanol and 2000 ml of toluene, and 91 g (3.95 moles) of small pieces of sodium were then placed into the flask with cooling. The mixture was slowly heated to effect reaction at 40° C. until the sodium completely dissolved. To the reaction mixture was added dropwise at about 50° C. a solution of 178 g (0.384 mole) of phosphonitrile chloride tetramer in 1000 ml of toluene. The mixture was refluxed for 4 hours for reaction, washed with water to remove the resulting sodium chloride, dried and then concentrated to obtain 620 g of a crude oily product. The product was distilled at 160° to 220° C./0.5 to 0.03 mmHg and thereafter fractionated by a high-temperature precision fractionator, HP-9000B (product of Shibata Kagaku Co., Ltd.). The fractions were analyzed by gas chromatography(GC), mass spectrum(MS), infrared(IR) absorption spectrum and proton nuclear magnetic resonance(NMR) spectrum to identify the following compounds produced.

$(CF_3CF_2CH_2O)l(HCF_2CF_2CF_2CF_2CH_2O)_{8-l}P_4N_4$

*(2,2,3,3,3-Pentafluoropropoxy)heptakis(1,1,5-trihydroperfluoropentyloxy)cyclotetraphosphonitrile (compound of the above formula wherein l is 1)

Boiling point: 209°~211° C./0.3 mmHg
  Refractive index (n, 20° C.): 1.3532
  Molecular weight: 1946

*Bis(2,2,3,3,3-pentafluoropropoxy)hexakis(1,1,5-trihydroperfluoropentyloxy)cyclotetraphosphonitrile (compound of the above formula wherein l is 2)

Boiling point: 201°~203° C./0.3 mmHg
  Refractive index (n, 20° C.): 1.3518
  Molecular weight: 1864

*Tris(2,2,3,3,3-pentafluoropropoxy)pentakis(1,1,5-trihydroperfluoropentyloxy)cyclotetraphosphonitrile (compound of the above formula wherein l is 3)

Boiling point: 195°~197° C./0.3 mmHg
  Refractive index (n, 20° C.): 1.3503
  Molecular weight: 1782

*Tetrakis(2,2,3,3,3-pentafluoropropoxy)tetrakis(1,1,5-trihydroperfluoropentyloxy)cyclotetraphosphonitrile (compound of the above formula wherein l is 4)

Boiling point: 189°~191° C./0.3 mmHg
  Refractive index (n, 20° C.): 1.3489
  Molecular weight: 1700

*Pentakis(2,2,3,3,3-pentafluoropropoxy)tris(1,1,5-trihydroperfluoropentyloxy)cyclotetraphosphonitrile (compound of the above formula wherein l is 5)

Boiling point: 179°~182° C./0.3 mmHg
  Refractive index (n, 20° C.): 1.3475
  Molecular weight: 1618

*Hexakis(2,2,3,3,3-pentafluoropropoxy)bis(1,1,5-trihydroperfluoropentyloxy)cyclotetraphosphonitrile (compound of the above formula wherein l is 6)

Boiling point: 168°~170° C./0.3 mmHg
  Refractive index (n, 20° C.): 1.3460
  Molecular weight: 1536

*Heptakis(2,2,3,3,3-pentafluoropropoxy)(1,1,5-trihydroperfluoropentyloxy)cyclotetraphosphonitrile (compound of the above formula wherein l is 7)
  Boiling point: 157°~159° C./0.3 mmHg
  Refractive index (n, 20° C.): 1.3446
  Molecular weight: 1454

Figure 1:
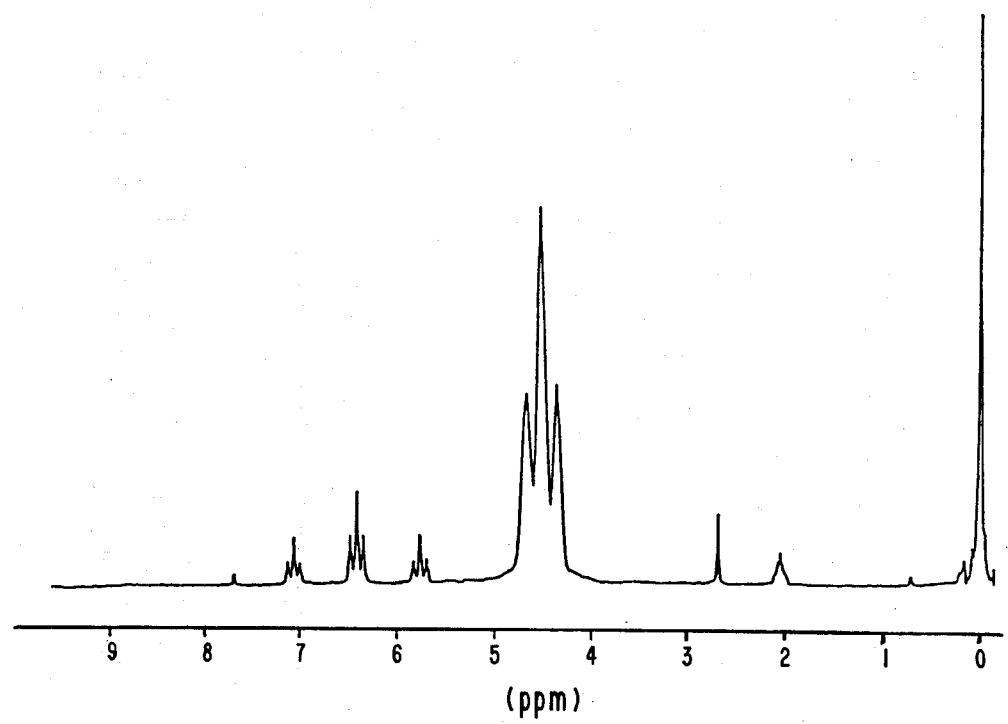
FIG. 1 is a diagram showing the proton NMR spectrum of one of the compounds obtained in Example 1.

FIG. 1 shows the proton NMR spectrum of pentakis(2,2,3,3,3-pentafluoropropoxy)tris(1,1,5-trihydroperfluoropentyloxy)cyclotetraphosphonitrile among other compounds obtained as above. The spectrum shows absorption characteristic of the 5-position hydrogen coupled with fluorine at 5.75, 6.40 and 7.05 ppm, with the sole difference in the integral strength ratio of absorption by the 1-position hydrogen at 4.5 ppm, compared with NMR spectra of other six compounds.

Figure 2:
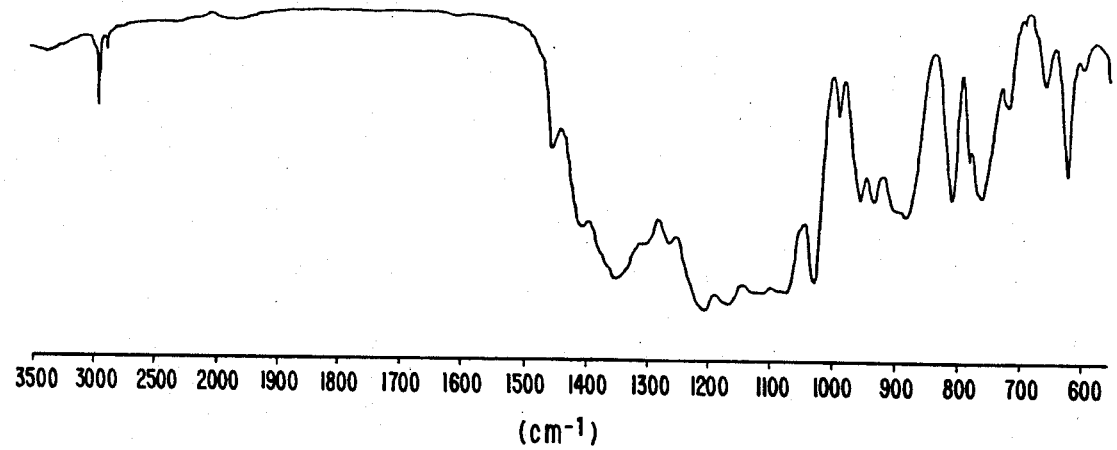
FIG. 2 is a diagram showing the IR absorption spectrum of one of the compounds obtained in Example 1.

FIG. 2 shows the IR absorption spectrum of tetrakis(2,2,3,3,3-pentafluoropropxy)tetrakis(1,1,5-trihydroperfluoropentyloxy)cyclotetraphosphonitrile obtained as above. The spectrum reveals absorption by the skeleton of cyclophosphonitrile tetramer at 1350 cm$^{-1}$.

Figure 3:
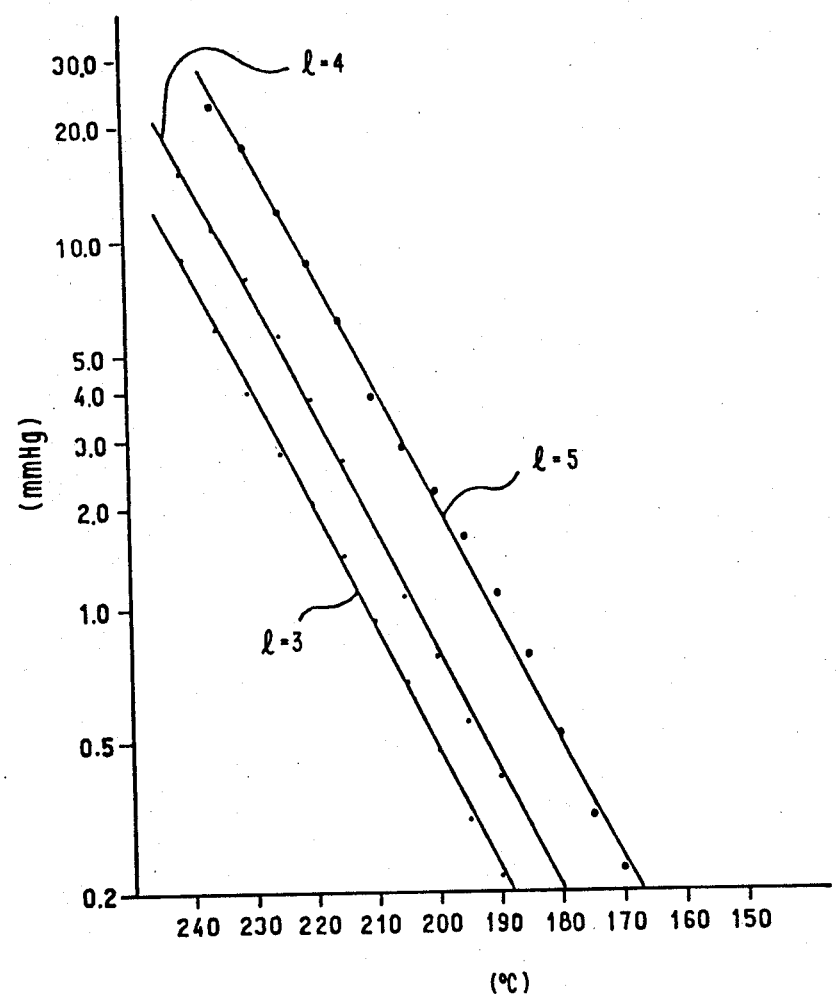
FIG. 3 is a diagram showing the vapor pressure charts of some of the compounds obtained in Example 1.

FIG. 3 is a diagram showing the vapor pressure charts of tris(2,2,3,3,3-pentafluoropropoxy)pentakis(1,1,5-trihydroperfluoropentyloxy)cyclotetraphosphonitrile, tetrakis(2,2,3,3,3-pentafluoropropoxy)tetrakis(1,1,5-trihydroperfluoropentyloxy)cyclotetraphosphonitrile and pentakis(2,2,3,3,3-pentafluoropropoxy)tris(1,1,5-trihydroperfluoropentyloxy)cyclotetraphosphonitrile.

EXAMPLE 2

A 605 g quantity of an oily crude product was obtained by preparing an alcoholate in the same manner as in Example 1, adding dropwise a solution of 178 g of phosphonitrile chloride trimer in toluene to the alcoholate, and reacting and after-treating the mixture in the same manner as in Example 1. The product was distilled at 130° to 195° C./0.75 to 0.03 mmHg and thereafter fractionated by the precision fractionator HP-9000B. The fractions were checked to identify the following compounds produced.

(CF$_3$CF$_2$CH$_2$O)l(HCF$_2$CF$_2$CF$_2$CF$_2$CH$_2$O)$_6$-lP$_3$N$_3$

*(2,2,3,3,-Pentafluoropropoxy)pentakis(1,1,5-trihydroperfluoropentyloxy)cyclotriphosphonitrile (compound of the above formula wherein l is 1)
  Boiling point: 178°~180° C./0.3 mmHg
  Refractive index (n, 20° C.): 1.3483
  Molecular weight: 1439

*Bis(2,2,3,3,3-pentafluoropropoxy)tetrakis(1,1,5-trihydroperfluoropentyloxy)cyclotriphosphonitrile (compound of the above formula wherein l is 2)
  Boiling point: 167°~169° C./0.3 mmHg
  Refractive index (n, 20° C.): 1.3459
  Molecular weight: 1357

*Tris(2,2,3,3,3-pentafluoropropoxy)tris(1,1,5-trihydroperfluoropentyloxy)cyclotriphosphonitrile (compound of the above formula wherein l is 3)
  Boiling point: 153°~155° C./0.3 mmHg
  Refractive index (n, 20° C.): 1.3436
  Molecular weight: 1275

*Tetrakis(2,2,3,3,3-pentafluoropropoxy)bis(1,1,5-trihydroperfluoropentyloxy)cyclotriphosphonitrile (compound of the above formula wherein l is 4)
  Boiling point: 142°~144° C./0.3 mmHg
  Refractive index (n, 20° C.): 1.3412
  Molecular weight: 1193

*Pentakis(2,2,3,3,3-pentafluoropropoxy)(1,1,5-trihydroperfluoropentyloxy)cyclotriphosphonitrile (compound of the above formula wherein l is 5)
  Boiling point: 130°~132° C./0.3 mmHg
  Refractive index (n, 20° C.): 1.3388
  Molecular weight: 1111

Figure 4:
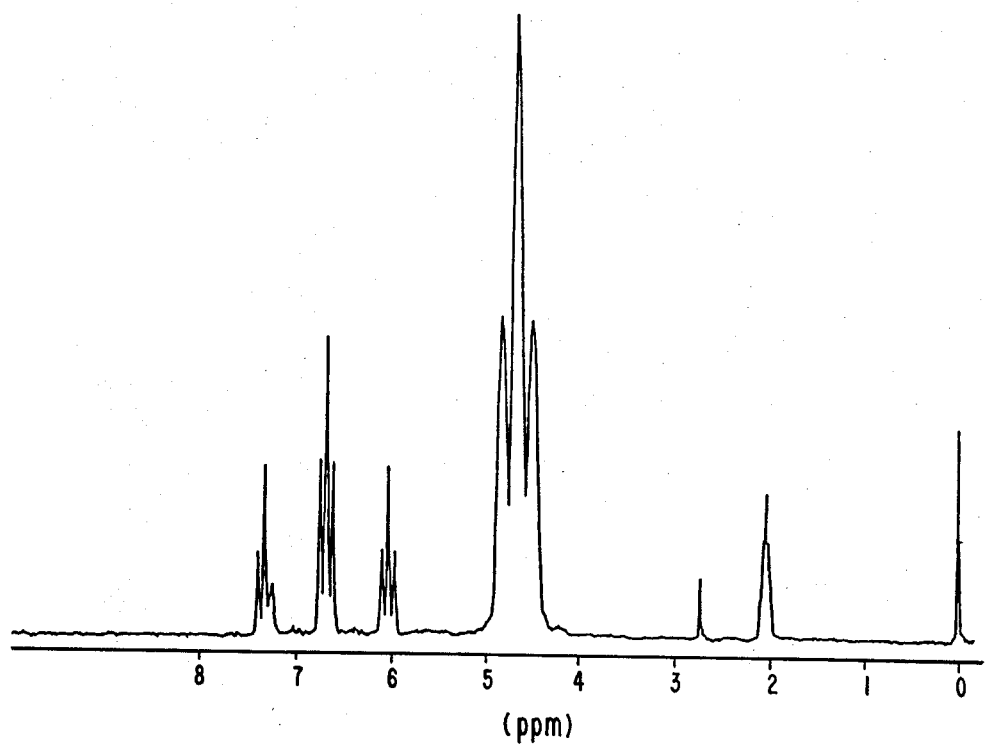
FIG. 4, FIG. 5 and FIG. 6 are diagrams showing proton NMR spectra of some compounds obtained in Example 2.
Figure 5:
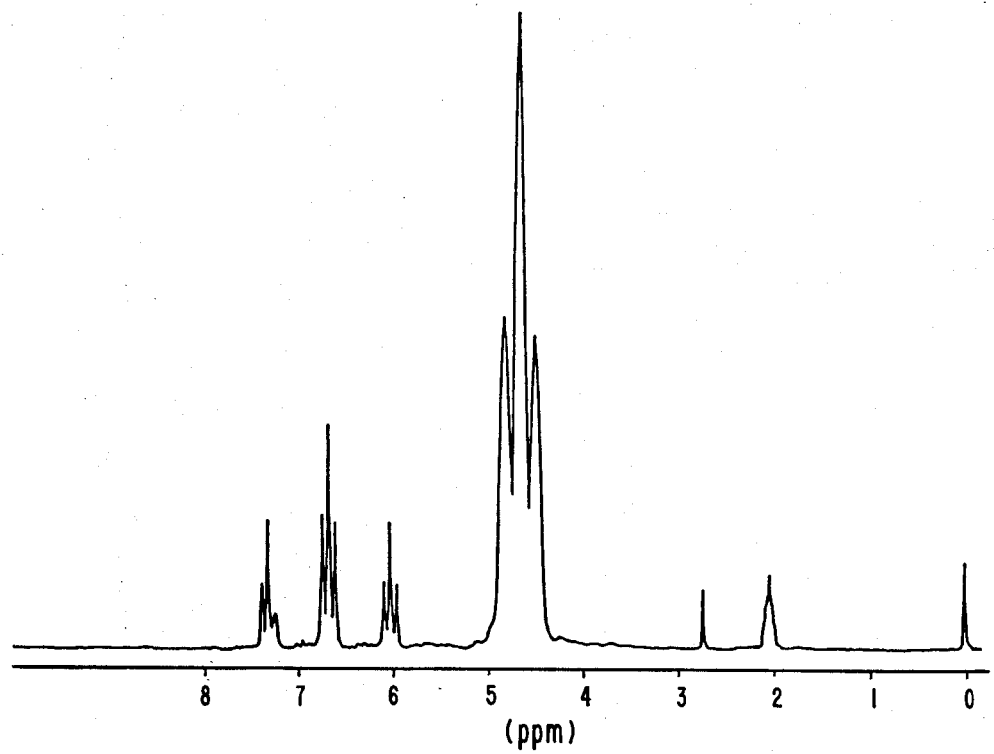
Figure 6:
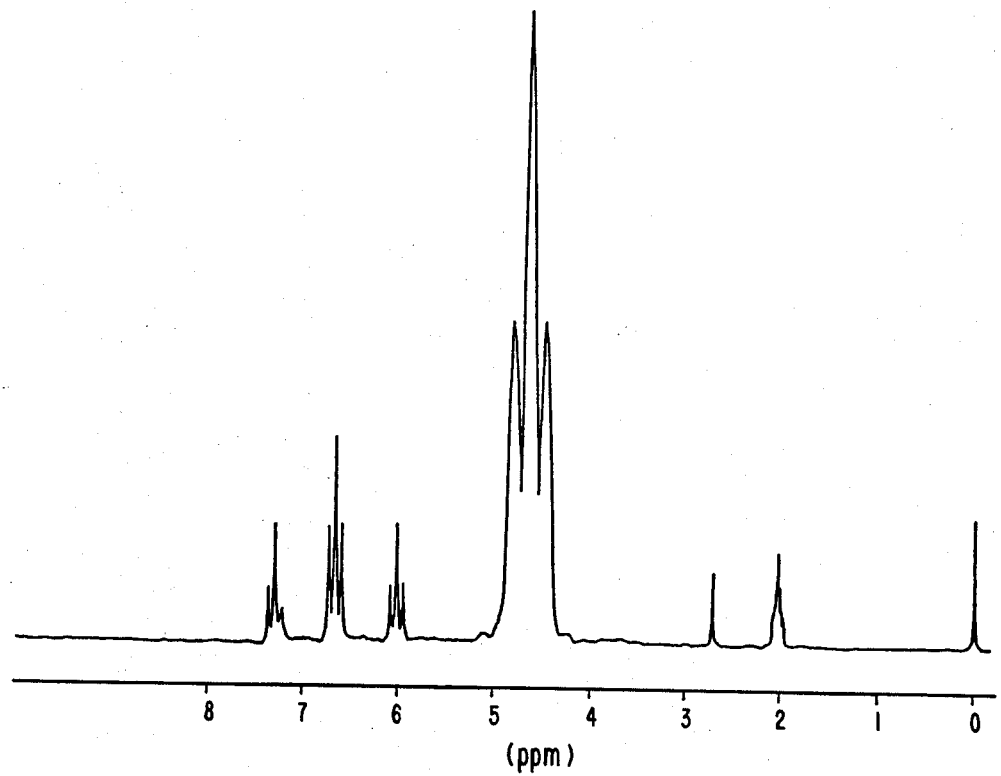
Figure 7:
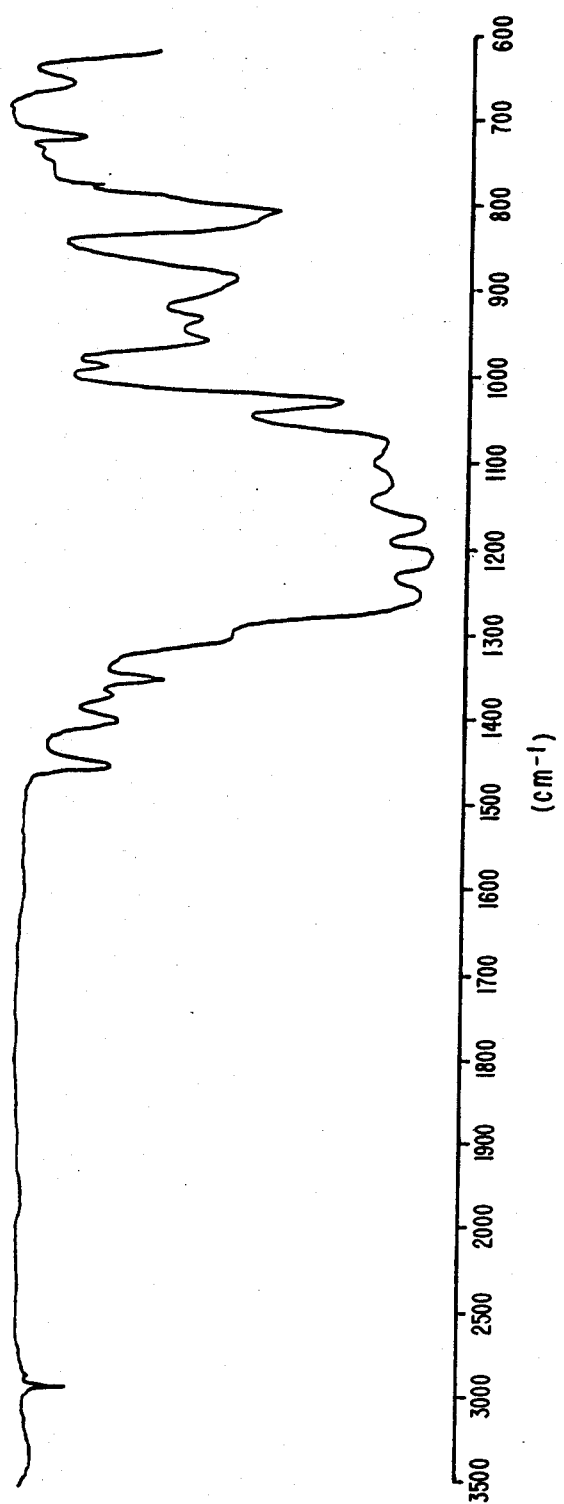
FIG. 7 is a diagram showing the IR absorption spectrum of one of the compounds obtained in Example 2.

FIGS. 4, 5 and 6 show the NMR spectra of bis(2,2,3,3,3-pentafluoropropoxy)tetrakis(1,1,5-trihydroperfluoropentyloxy)cyclotriphosphonitrile, tris(2,2,3,3,3-pentafluoropropoxy)tris(1,1,5-trihydroperfluoropentyloxy)cyclotriphosphonitrile and tetrakis(2,2,3,3,3-pentafluoropropoxy)bis(1,1,5-trihydroperfluoropentyloxy)cyclotriphosphonitrile, respectively, among other compounds obtained as above. Further FIG. 7 shows the IR absorption spectrum of tetrakis(2,2,3,3,3-pentafluoropropoxy)bis(1,1,5-trihydroperfluoropentyloxy)cyclotriphosphonitrile.

EXAMPLE 3

Figure 8:
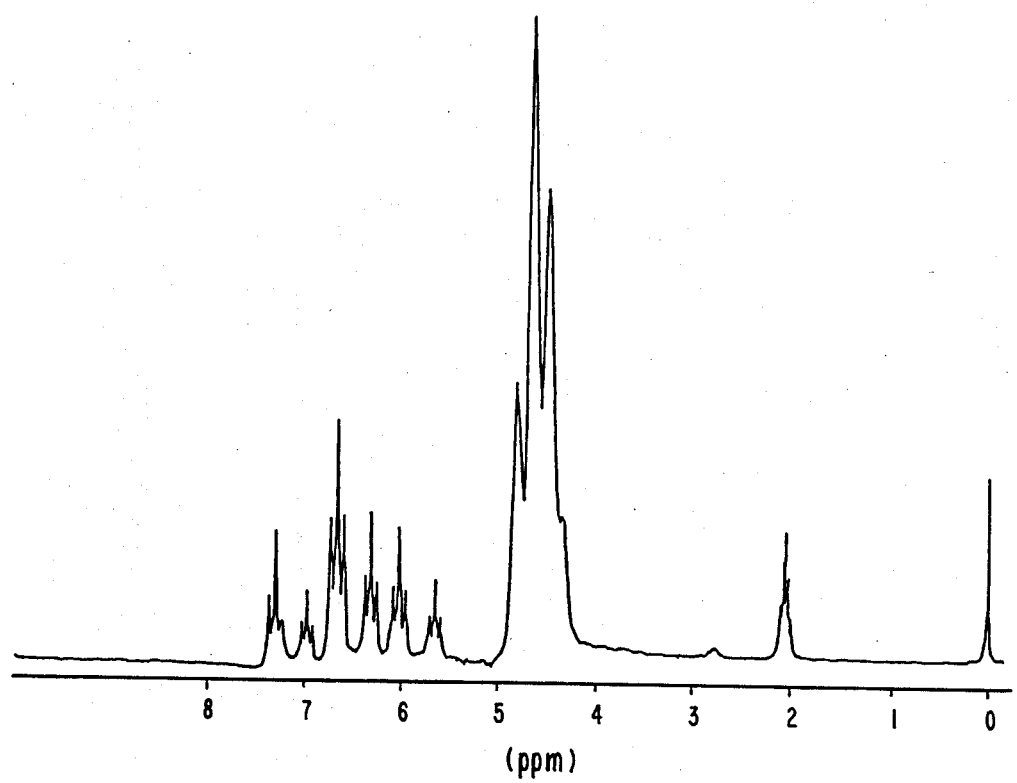
FIG. 8 is a diagram showing the proton NMR spectrum of the compound obtained in Example 3.
Figure 9:
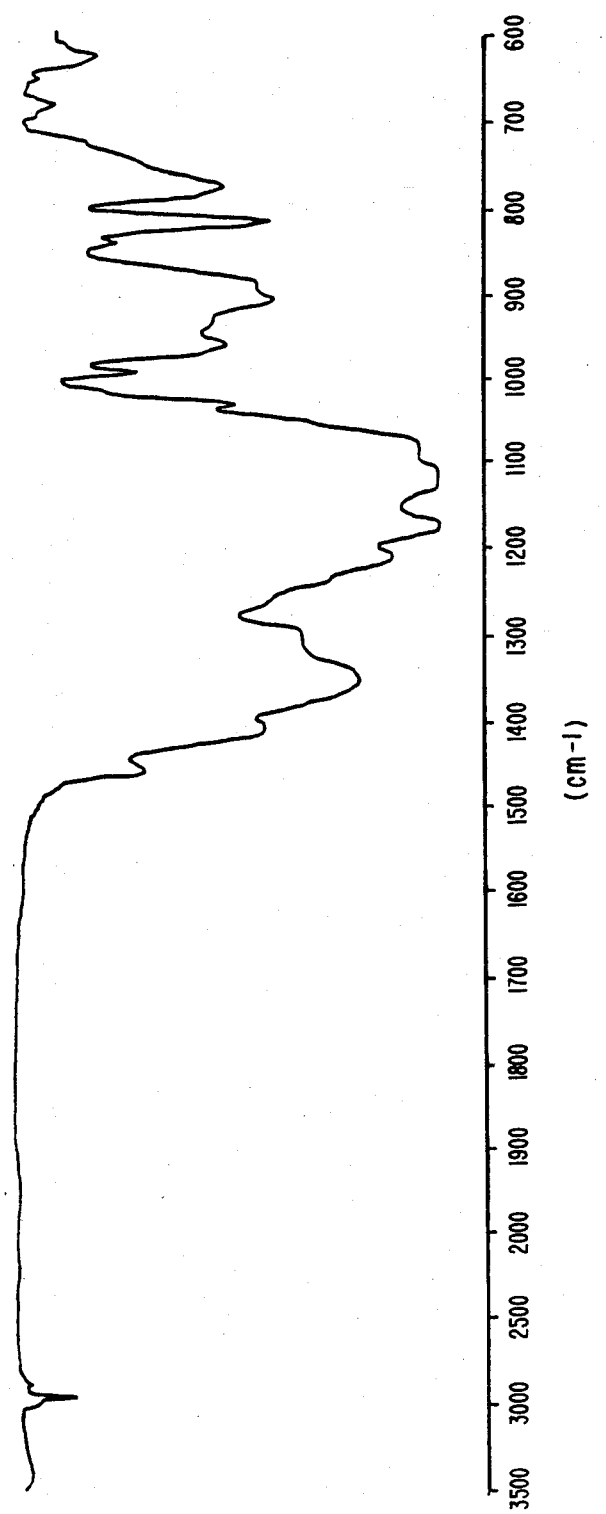
FIG. 9 is a diagram showing the IR absorption spectrum of the compound obtained in Example 3.

Into the same reactor as used in Example 1 were placed 178 g (0.384 mole) of phosphonitrile chloride tetramer and 1000 ml of toluene, and the tetramer was completely dissolved. To the solution was added dropwise an alcoholate prepared from 480 g (2.06 moles) of 1,1,5-trihydroperfluoropentanol and 45.5 g (1.98 moles) of sodium in 1000 ml of toluene. The mixture was reacted at 50° C. for 4 hours. To the reaction mixture was added dropwise an alcoholate separately prepared from 155 g (1.03 moles) of 2,2,3,3,3-pentafluoropropanol, 136 g (1.03 moles) of 1,1,3-trihydrotetrafluoropropanol and 45.5 g (1.98 moles) of sodium in 1000 ml of toluene, followed by reaction at 50° C. for 4 hours. The reaction mixture was thereafter treated, distilled and precision-fractionated in the same manner as in Example 1, giving 120 g of a fraction at 193° to 195° C./0.3 mmHg. The compound obtained was identified as bis(2,2,3,3,3-pentafluoropropoxy)bis(1,1,3trihydroperfluoropropoxy)tetrakis(1,1,5-trihydroperfluoropentyloxy)cyclotetraphosphonitrile by gas chromatography, mass analysis and proton NMR spectrum. The compound had a refractive index of 1.3567 at 20° C. FIG. 8 shows the proton NMR spectrum of the product, and FIG. 9 the IR absorption spectrum thereof.

EXAMPLE 4

Into a four-necked flask equipped with a condenser, stirrer and thermometer were placed 155 g (1.03 moles) of 2,2,3,3,3-pentafluoropropanol, 240 g (1.03 moles) of 1,1,5-trihydrooctafluoropentanol and 1000 ml of toluene. Small pieces of sodium (45.3 g, 1.97 moles) were further placed into the flask with cooling. The mixture was reacted at 40° C. for 4 hours until the sodium completely dissolved. To the reaction mixture was added dropwise at about 50° C. a solution of 89 g (0.192 mole) of phosphonitrile chloride tetramer in 500 ml of toluene, and the mixture was refluxed for 4 hours for reaction. The reaction mixture was washed with water to remove the resulting sodium chloride, dried and concentrated to give 310 g of an oily crude product. The product was distilled at a reduced pressure to obtain 260 g of a fraction at 160° to 193° C./0.03 mmHg. GC and GC-MS analysis revealed that the colorless transparent oily product obtained was a mixture of seven compounds of the formula (1) wherein n is 4, m is 2, and l is 1 to 7, the proportions being 1.6% for l=1, 8.6% for l=2, 22.9% for l=3, 32.7% for l=4, 23.3% for l=5, 8.5% for l=6 and 1.5% for l=7. This substance was 1.746 in specific gravity (20° C.), 204 cps in viscosity (40° C.), 1 mmHg/188° C. in vapor pressure and −37.5° C. in pour point. This substance will be referred to as "compound A" hereinafer.

EXAMPLE 5

An alcoholate was prepared in the same manner as in Example 1 from a mixture of 63 g of 2,2,3,3,3-pentafluoropropanol, 56 g of 1,1,3-trihydrotetrafluoropropanol and 98 g of 1,1,5-trihydrooctafluoropentanol and then reacted with phosphonitrile chloride tetramer. The reaction mixture was treated in the same manner as in Example 1 to collect 235 g of a fraction at 160° to 185° C./0.03 mmHg. The product was a colorless transparent oily substance (hereinafter referred to as "compound B") which was 1.73 in specific gravity (20° C.), 285 cps in viscosity (40° C.) and −35° C. in pour point. The $^1$H-NMR integral values accurately measured revealed that compound B had the average values of l=0.59 and m=1.55.

EXAMPLE 6

A 155 g quantity of 2,2,3,3,3-pentafluoropropanol was added to 240 g of a mixture of telomeric fluorinated alcohols represented by the formula H(CF$_2$CF$_2$)$_m$CH$_2$OH (in the proportions of 33, 42, 17, 5 and 3% for m=1, 2, 3, 4 and 5, respectively, the average m value being 2.03 as determined by GC analysis) to prepare an alcoholate, which was then reacted with 89 g of a phosphonitrile chloride mixture (in the proportions of 69, 16, 7 and 8% for n=3, 4, 5 and 6 or greater, respectively, as determined by GC analysis) to obtain 210 g of a fraction at 167° to 220° C./0.03 mmHg. The product (hereinafter referred to as "compound C") was 1.74 in specific gravity (20° C.), 340 cps in viscosity (40° C.) and −35° C. in pour point.

REFERENCE EXAMPLE 1

Compound A was poured into a mechanical vacuum pump completely cleaned with a solvent. The oil temperature, degree of vacuum and power consumption were measured on start-up and during one-week continuous operation. Table 1 shows the results, which reveal that the compound is usable as a vacuum pump oil without any problem.

TABLE 1

| Hour meter (min) | Watt-hour meter (kWh) | Power consumption (kW) | Oil temp. (°C.) | Room temp. (°C.) | Vacuum (Torr) |
| --- | --- | --- | --- | --- | --- |
| 0 | 288.14 | | 28 | 28 | |
| 2 | 288.16 | ↓ | 30 | | 0.01 |
| 4 | 288.17 | 0.45 | 37.5 | | 0.008 |
| 7 | 288.19 | ↓ | 45 | | 0.005 |
| 10 | 288.21 | 0.40 | 50 | | 0.007 |
| 20 | 288.27 | 0.36 | 60 | | 0.005 |
| 30 | 288.32 | 0.30 | 66 | | 0.005 |
| 40 | 288.37 | 0.30 | 69 | 30 | 0.005 |
| 50 | 288.42 | 0.30 | 70 | | 0.005 |
| 60 | 288.47 | 0.30 | 72 | | 0.005 |
| 70 | 288.52 | 0.30 | 74 | 30 | 0.006 |
| 80 | 288.57 | 0.30 | 74.5 | | 0.006 |
| 90 | 288.62 | 0.30 | 75 | | 0.005 |
| 100 | 288.67 | 0.30 | 75.5 | | 0.006 |
| 105 | 288.69 | ↓ | 75 | | 0.005 |
| 110 | 288.71 | 0.24 | 74 | | 0.005 |
| 110 | 0.57 | 0.31 | | | |
| 763.85 | 239.11 | | | | |
| 770.65 | 241.05 | 0.28 | 75 | 30 | 0.005 |
| 785.9 | 245.33 | 0.28 | 74 | 30 | 0.004 |
| 794.6 | 247.76 | 0.28 | 76 | 36 | 0.005 |
| 813.95 | 253.15 | 0.28 | 77 | 36 | 0.004 |
| 818.2 | 254.33 | 0.28 | 75 | 34 | 0.004 |
| 833.45 | 258.54 | 0.28 | 77 | 37 | 0.004 |
| 843.05 | 261.27 | 0.28 | 74 | 30 | 0.004 |
| 905.4 | 278.7 | 0.28 | 76 | 34 | 0.003 |
| 914.3 | 281.23 | 0.28 | 74 | 38 | 0.005 |
| 939.05 | 288.14 | 0.28 | 75 | 30 | 0.005 |
| 175.2 hr (7.3 day) | 49.03 | 0.28 | | | |

REFERENCE EXAMPLE 2

Compound B was poured into a mechanical vacuum pump completely cleaned with a solvent, and the pump was used for operating an experimental plasma generator wherein a mixture of Flon-14 and hydrogen was used. No abnormalities were found in the motor current value during operation for 30 days. When the oil was drawn off and checked, a small amount of reddish brown liquid was found on the oil. The oil had a viscosity of 280 cps at 40° C., while the oil before use had a viscosity of 285 cps at the same temperature, hence almost no change in viscosity. IR, NMR and MS (mass spectrum) analyses revealed no difference between the used oil and the fresh oil. The reddish brown liquid, which appeared attributable to the plasma or the etched work, caused no trouble to the operation of the rotary pump.

REFERENCE EXAMPLE 3

A mechanical vacuum pump (exhaust rate 960 liters/min, amount of oil 2.2 liters) was operated with compound A placed therein for a dry etching apparatus for etching silicon substrates with use of a mixture of Flon-14 and oxygen in a semiconductor manufacturing process.

After operating the pump for 3 weeks, the oil was drawn off and checked. Although the oil was found to be turbid and to contain a small amount of reddish brown substance suspended in the upper portion of the oil, the oil itself was 200 cps in viscosity (40° C.). Since the oil before use was 204 cps in viscosity (40° C.), almost no change occurred in viscosity. IR, NMR and MS spectra revealed no difference between the used oil and the fresh oil. These results show that compound A has outstanding resistance to the above active gas mixture. The turbidity and the reddish brown suspended substance were attributable to the presence of extraneous matter such as etched particles.

REFERENCE EXAMPLE 4

(Evaluation of Compatibility with Resin)

Fluorine rubber which is frequently used for applciations where resistance to chemicals is required was tested for resistance to the present compound. A Viton O-Ring (V#4640, 4DG-30), product of Asahi Chemicals Co., Ltd., was immersed in compound A at 80° C. for 15 days and thereafter checked for the resulting change in volume. The volume increase ratio was 2.2%. For comparison, the above procedure was repeated using in place of compound A hexakis(1,1,5-trihydrooctafluoropentyl)triphosphonitrilate ("active gas resistant rotary pump oil A" disclosed in Japanese Unexamined Patent Publication No. 1983-164698). The volume increase ratio was 9.55%.

The above results indicate that compound A does not substantially swell Viton and is suited to use with the resin.

REFERENCE EXAMPLE 5

(Evaluation of Thermal Stability)

Compound A, "active gas resistant rotary pump oil A" disclosed in Japanese Unexamined Patent Publication No. 1983-164698, or commercial high vacuum oil of the mineral oil type, "MR-200" was heated at 150° C. in contact with air within a heat-resistant glass container and checked for changes. Compound A became slightly turbid in 20 days but thereafter remained almost unchanged, whereas the active gas resistant rotary pump oil A became turbid in white in 10 days and thereafter gradually became more turbid. MR-200 became light brown one hour after the start of heating and thereafter increased in color density with time.

The above results reveal that compound A has good heat resistance.

We claim:

1. A fluoroalkoxy cyclic phosphonitrile ester represented by the formula (1)

$$[H(CF_2CF_2)_m CH_2O]_{2n-l}[CF_3CF_2CH_2O]_l P_n N_n \quad (1)$$

wherein $(CF_2CF_2)m$ is a single segment of the unit $(CF_2CF_2)$ multiplied by an integer or indicates conjoint presence of segments having different chain lengths and each comprising the unit $(CF_2CF_2)$ multiplied by an integer, m is 2 in the case of the single segment or, in the case of the presence of segments of different chain lengths, represents the average of the chain lengths, means the average number of repeating units $(CF_2CF_2)$ and is in the range of $1.3 \leq m \leq 2.8$, l is in the range of $2n-1 \geq l \geq 1$, and n is the number of repeating PN units of the phosphonitrile cyclic skeleton, or represents the average number of repeating PN units and is a real number in the range of $3 \leq n \leq 4.3$ when rings of different numbers of repeating units are conjointly present, said ester being fluid at room temperature.

2. A fluoroalkoxy cyclic tetraphosphonitrile ester as defined in claim 1 wherein m is 2 to indicate the presence of the segment of single chain length, l is in the range of $2n-1 \geq l \geq 1$, and n is 4.

* * * * *